United States Patent [19]

Steber et al.

[11] Patent Number: 4,837,381

[45] Date of Patent: Jun. 6, 1989

[54] COMPOSITIONS FOR PARENTERAL ADMINISTRATION AND THEIR USE

[75] Inventors: William Steber, Ledgewood; Richard Fishbein, Skillman, both of N.J.; Susan M. Cady, Yardley, Pa.

[73] Assignee: American Cyanamid Company, Stamford, Conn.

[21] Appl. No.: 78,926

[22] Filed: Jul. 31, 1987

Related U.S. Application Data

[63] Continuation-in-part of Ser. No. 895,608, Aug. 11, 1986, abandoned.

[51] Int. Cl.[4] .................................................. A61K 9/50
[52] U.S. Cl. ........................................ 424/502; 424/484; 424/500; 424/499; 424/95; 424/438
[58] Field of Search ............... 424/502, 438, 439, 442, 424/95

[56] References Cited

U.S. PATENT DOCUMENTS

| | | | |
|---|---|---|---|
| 3,147,187 | 9/1964 | Playfair | 424/502 |
| 4,452,775 | 6/1984 | Kent | 424/430 |
| 4,483,847 | 11/1984 | Augart | 424/470 |
| 4,568,536 | 2/1986 | Kronenthal et al. | 424/484 |
| 4,568,559 | 2/1986 | Nuwayser et al. | 424/497 |
| 4,650,787 | 3/1987 | Schally et al. | 514/11 |
| 4,696,914 | 9/1987 | Russe et al. | 514/19 |

FOREIGN PATENT DOCUMENTS

| | | |
|---|---|---|
| 0085036 | 8/1983 | European Pat. Off. . |
| 0205051 | 12/1986 | European Pat. Off. . |
| 2406621 | 8/1974 | Fed. Rep. of Germany . |

*Primary Examiner*—William R. Dixon, Jr.
*Assistant Examiner*—Jerry D. Johnson
*Attorney, Agent, or Firm*—Alice C. Brennan

[57] ABSTRACT

The invention is a microsphere composition of fat or wax or mixture thereof and a biologically active protein, peptide or polypeptide suitable for parenteral administration. The invention is also a slow release composition of fat or wax or mixture thereof and a biologically active protein, peptide or polypeptide suitable for parenteral administration. The invention also relates to methods for increasing and maintaining increased levels of growth hormone in the blood of treated animals for extended periods of time, increasing weight gains in animals, and increasing milk production of lactating animals by the administration of compositions of the invention.

25 Claims, No Drawings

COMPOSITIONS FOR PARENTERAL ADMINISTRATION AND THEIR USE

This application is a continuation-in-part of application Serial No. 895,608, filed August 1, 1986 now abandoned.

BACKGROUND OF THE INVENTION

Recent developments in the administration of drugs in forms which control the release of the drug include biodegradable polylactide implants such as those disclosed in European Patent Application No. 82300416.3; beeswax implants for the administration of growth hormone (oGH) as described by S. L. Davies, et al, in *The Journal of Dairy Science*, Vol. 66, No. 9, pp 1980–1981 (1983); a cholesterol matrix delivery system for the sustained release of macromolecules, including a variety of growth hormones, which is described in U.S. Pat. No. 4,452,775; subdermal sustained release implants containing microencapsulated drug in a matrix as described in U.K. Pat. No. GB 2,103,927; slow release implants of Zn-DTPA as described in chemical abstracts CA 90(20):15704IV; and orally administered composition of morphine in lipids as described by K. S. Chang, et. al., in *J. Pharm. Sci.*, 69(4), 466–9. Injectable sustained release compositions include biodegradable polymer microcapsules containing aqueous solutions of polypeptides which are described in European Patent Application No. 81305426.9, a crystalline carbohydrate nanosphere matrix described by U. Schroder, *J. Immunological Methods* 70, 127–132 (1984), and prolonged release nonaqueous compositions of polypeptides which are preferably associated with metals or metal compounds which may additionally contain antihydration agents dispersed in biocompatible oils, which are described in European Patent Application No. 85870135.2, published Apr. 4, 1986.

Methods for the preparation of pharmaceutical compositions include, a process for the preparation of pharmaceutical compositions which exhibit retarded liberation of active material utilizing both a high melting and a low melting lipid of lipoid and embedding the active ingredient at a temperature greater than the temperature of the low melting component prior to tableting, which is described in U.S. Pat. No. 4,483,847; and a process for the preparation of amino acid containing microcapsules which is described in U.S. Pat. No. 3,726,805. A general process for encapsulating or coating solid particles or viscous liquid droplets is described in International Patent Application PCT/US No. 85/00827 and a method for the preparation of wax-particles is described in UK patent application GB No. 2,088,274.

It is clear from the above references that there is considerable interest in providing dosage forms of biologically active substances which release the substance in a controlled manner and, thus, reduce the frequency of administration.

The development of sustained release compositions of biologically active macromolecules presents special problems due to their complex modes of action and intricate structures. The development of sustained release compositions containing biologically active macromolecules such as growth hormones, which do not interfere and/or interact with these hormones resulting in compositions which are either inactive or do not provide the expected level of biological response, is required. It is an object of the present invention to provide compositions of biologically active proteins, peptides and polypeptides such as growth hormones, which are suitable for parenteral administration. It is another object of this invention to provide a method of increasing and maintaining increased levels of growth hormones in the blood of treated animals and humans for extended periods of time and obtaining beneficial effects such as increasing weight gains, increasing milk production in lactating animals, increasing growth rate, increasing feed efficiency, increasing muscle size, decreasing body fat and improving the lean meat to fat ratio by parenteral administration of the compositions of the invention.

SUMMARY OF THE INVENTION

The invention is a microsphere composition of a fat or wax or mixtures thereof and a biologically active protein, peptide or polypeptide which is administered by dispersion in a pharmaceutically and pharmacologically acceptable liquid vehicle. The invention is also a slow release composition of a fat or wax or mixtures thereof, and a biologically active protein, peptide or polypeptide dispersed in a pharmaceutically and pharmacologically acceptable liquid vehicle. There may be hydrophobic interaction, bonding or coating of the active ingredient to the fat or wax.

The compositions are suitable for parenteral administration to animals. The biologically active proteins, peptides or polypeptides include growth hormones, somatomedins, growth factors, and other biologically active fragments or derivatives thereof.

The invention includes a method for increasing milk production in animals, particularly dairy cows comprising parenterally administering compositions of the invention to the cows. The invention also includes a method for elevating and maintaining elevated blood levels of biologically active proteins, peptides or polypeptides in humans or animals comprising parenterally administering compositions of the inventions.

Waxes and fats which are suitable for use in the compositions of this invention in general have melting points higher than 40° C. The wax of the invention may be defined as set forth in Hawley's *The Condensed Chemical Dictionary*, Eleventh Edition, as a low-melting organic mixture or compound of high molecular weight, solid at room temperature and generally similar in composition to fats and oils except that it contains no glycerides. Some are hydrocarbons; others are esters of fatty acids and alcohols. These compounds include saturated or unsaturated long chain $C_{10}$–$C_{24}$ fatty acids, alcohols, esters, salts, ethers or mixtures thereof. They are classed among the lipids. Waxes are thermoplastic, but since they are not high polymers, they are not considered in the family of plastics. Common properties are water repellency; smooth texture; nontoxicity; freedom from objectionable odor and color. They are combustible and have good dielectric properties. They are soluble in most organic solvents and are insoluble in water. The major types are as follows:

I. Natural
  1. Animal (beeswax, lanolin, shellac wax, Chinese insect wax)
  2. Vegetable (carnauba, candelilla, bayberry, sugar cane)
  3. Mineral
    (a) Fossil or earth waxes (ozocerite, ceresin, montan)

(b) petroleum waxes (paraffin, microcrystalline) (slack or scale wax)

II. Synthetic
1. Ethylenic polymers and polyol ether-esters ("Carbowax," sorbitol)
2. Chlorinated naphthalenes ("Halowax")
3. Hydrocarbon type via Ficher-Tropsch synthesis The fat of the invention may be defined as set forth in Hawley's *The Condensed Chemical Dictionary*, Eleventh Edition, as a glyceryl ester of higher fatty acids such as stearic and palmitic. Such esters and their mixtures are solids at room temperatures and exhibit crystalline structure. Lard and tallow are examples. There is no chemical difference between a fat and an oil, the only distinction being that fats are solid at room temperature and oils are liquid. The term "fat" usually refers to triglycerides specifically, whereas "lipid" is all-inclusive.

The fat is preferably composed of mono-, di-or triglyceryl esters of long chain $C_{10}$–$C_{24}$ fatty acids. The mono-, di-, or triglycerides are composed predominantly of stearates, palmitates, laurates, linoleates, linolenates, oleates, and residues or mixtures thereof, having melting points greater than 50° C. being most preferred. Glyceryl tristearate is a most preferred fat. Additionally, lipophilic salts of fatty acids such as magnesium stearate and the like are also suitable.

The microspheres of the invention are dispersed in a pharmaceutically and pharmacologically acceptable liquid to obtain a slow release composition for parenteral administration. The vehicle may be aqueous buffered systems or oil systems. The oil may be derived from animal or vegetable sources or be synthetic. Preferred oils include neutral mono-, di-or triglyceride liquid or mixtures thereof. A neutral oil is one containing no residual acid. Vehicles suitable for use in the compositions of this invention include aqueous systems such as buffered salines; organic solvents such as glycols and alcohols; and water immiscible liquids such as oils, depending upon the solubility of the active ingredient being administered.

Biologically active proteins, peptides and polypeptides suitable for administration in the compositions of the invention include growth hormones, somatomedins, growth factors, and other biologically active fragments and derivatives thereof. Preferred proteins include bovine, ovine, equine, porcine, avian, and human growth hormones; and is meant to encompass those which are of natural, synthetic, recombinant or biosynthetic origin. Additionally, metals or metal compounds associated with biologically active proteins, peptides and polypeptides, as well as acid salts, derivatives and complexes and antihydrating agents are suitable for incorporation into the compositions of the invention.

Stabilizers, preservatives, surfactants, salts, buffers or mixtures thereof may be included in the compositions of the invention. Preferred stabilizers include dehydroacetic acid, salicylanilide, sorbic acid, boric acid, benzoic acid, and salts thereof; sodium nitrite and sodium nitrate. The amounts of said materials suitable for use in the invention range from about 0.1% to 20% on a weight basis.

Preferred surfactants for use in compositions of the invention containing biologically active macromolecules are non-ionic in nature such as polyoxyethylene sorbitan mono-oleate (20 moles ethoxylation), and block copolymers of ethylene oxide and propylene oxide. The amounts of surfactants suitable for use in the invention range from about 0.1% to 10.0% on a weight basis being preferred.

Uniquely, it has been found that increased blood levels of growth hormones may be obtained and maintained for extended periods of time, as can increased weight gains and increased milk production in lactating animals by injecting animals with the compositions of the invention in a suitable vehicle. Elevated blood levels of the biologically active proteins, peptides and polypeptides are generally observed and associated with beneficial and/or therapeutic effects. The effects include weight gain, increased growth rate, increased milk production in lactating animals and associated increased availability milk to nursing offspring of treated animals, improved muscle size, improved feed efficiency, decreased body fat and improved the lean meat to fat ratio. Maintaining the elevated blood levels is an indication of the slow release of the active ingredient. Properties such as increased milk production, growth rate, improved feed efficiency and increased lean meat are generally observed when elevated blood levels of the active ingredient are maintained. The invention includes the use of the compositions herein to improve milk production, increase growth rate, improve feed efficiency, increase lean meat in animals, increase and maintain levels of hormones in the blood stream of animals.

A preferred embodiment of this invention involves the incorporation of the biologically active protein, peptide or polypeptide in fat or wax microspheres which may optionally also contain some or all of the excipients described above, which are then dispersed in the vehicle. The microspheres, preferably fat microspheres, may be up to 1,000 microns in diameter, with a weight average size range of 25 microns to 300 microns being preferred for parenteral administration. Microspheres containing up to about 70% of a biologically active protein, peptide or polypeptide exhibit sustained release for various periods of time depending upon the solubility of the active ingredient and the nature of the wax or fat, surfactant, buffer and vehicle employed.

The invention in its broadest sense is a slow release composition comprising a mixture of the fat or wax or mixture thereof and a biologically active protein, peptide or polypeptide drug dispersed in a pharmaceutically and pharmacologically acceptable vehicle. Microspheres and coated protein particles may be present in the slow release composition. The composition may be the protein dissolved in the fat or wax or there may be hydrophobic interaction or bonding of the active ingredient to the fat or wax. For the administration of hormone, compositions comprising on a weight basis about 1% to 30% of growth hormone, somatomedin, growth factor or biologically active fragment or derivative thereof preferably having a weight average particle size less than 20 microns; about 5% to 60% and preferably about 10% to 48% of the fat, wax or mixture thereof; optionally containing up to about 15% of excipients such as surfactants, stabilizers, preservatives, salts or buffers or mixtures thereof with sufficient amount of a pharmaceutically and pharmacologically acceptable liquid vehicle to total 100%. The vehicle is again the aqueous buffered or oil system described above.

For the parenteral administration of growth hormones such as bovine growth hormone, microspheres comprising on a weight basis of about 5% to 40% of the solid hormone preferably having a weight average particle size of less than 20 microns, containing up to about 20% of the other excipients as described above in about 40% of 95% of fat or wax or a mixture thereof; having a weight average particle size range of 25 microns to 300 microns have demonstrated sustained release of the hormone and sustained increases in milk production in lactating dairy cows for about two weeks and are preferred. These preferred compositions have demonstrated increased milk production which is comparable to that obtained by daily injection of bovine growth hormone.

For the administration of compositions containing water soluble proteins, peptides or polypeptides such as bovine growth hormone, water immiscible liquids are preferred, with oils or liquid fats and water immiscible alcohols and glycols and mixtures thereof being more preferred. The vehicles are chosen so as to both disperse and coat the mixture of microspheres and also to provide an acceptable viscosity of the injection mixture using HLB values (Hydrophilic Lipophilic Balance) and viscosity as criteria for their selection.

On this basis, fatty acid glycerides and blends thereof which are liquid at ambient temperatures including synthetic oils; vegetable oils, such as olive, sesame seed, peanut, sunflower seed, soybean, cottonseed, corn, safflower, palm, rapeseed and coconut; animal oils such as fish oils, fish liver oils, sperm oils; or fractions derived therefrom; and mixtures thereof; having HLB values in a range of 1 to 5 and viscosities in a range of from 10 cps to 1000 cps as measured with a Brookfield viscometer RTV using a #1 spindle find utility vehicles for compositions of the present invention.

The microspheres of the invention may be prepared by incorporating the active ingredient, having the desired particle size, and other excipients with a molten fat, wax or mixture thereof and then forming microspheres of the resulting mixture by a variety of techniques such as emulsifying or atomizing the mixture or by processing the mixture of ingredients and molten fat, wax or mixture thereof mechanically and cooling, for example utilizing a centrifugal disc, as described in International Patent Application PCT/US No. 85/00827. Alternatively, the mixture of active ingredients, excipients and fat, waxes and mixtures thereof may be cooled to give a solid which may then be processed by procedures such as milling, grinding and the like.

Mixtures of the invention suitable for injection are readily prepared by dispersing the protein, peptide or polypeptide, excipients, fat, wax or mixture thereof at elevated temperatures directly in the vehicle and cooling. The invention is further illustrated by the following non-limiting examples.

EXAMPLE 1

Preparation of injectable microspheres for the parenteral administration of bovine growth hormone 1. Preparation of bovine growth hormone and additives in a size range suitable for incorporation in microspheres by spray drying may be accomplished by dissolving bovine growth hormone in dilute ammonium hydroxide solution and then adding the desired salt solutions such as sodium benzoate. A nonionic surfactant such as a block copolymer of ethylene oxide and propylene oxide is added and allowed to dissolve with constant gentle mixing. The solution is then spray-dried in a Buchi mini spray dryer, model #190.

2. Preparation of injectable microspheres. A homogeneous mixture of active ingredient and additives in the molten fat, wax or mixture thereof is prepared and the resulting mixture sprayed through an air/liquid spray nozzle equipped with a heated jacket to maintain the incoming air and the molten phase at a temperature above the melting point. The microspheres are formed as the molten droplets cool and are collected on a series of sieves in the desired size range of about 45 to 180 microns and retained for use. Those microspheres which are not of the desired size range are collected for recycling. Alternatively, the homogeneous mixture may be fed onto a centrifugal disc and the microspheres thus formed are collected as above, or the molten mixture may be cooled and milled to the desired average particle size range.

Utilizing the above procedure with the materials listed in Table I below yields the injectable microsphere compositions listed in Table II below:

TABLE I

| Name | Designation |
| --- | --- |
| Glyceryl Monostearate | GMS |
| Glyceryl Distearate | GDS |
| Glyceryl Tristearate | GTS |
| Glyceryl Trilaurate | GTL |
| Soya Oil | Soya Oil |
| Beeswax | Beeswax |
| Carnauba Wax | Carnuaba |
| Sodium Laurate | NaLaurate |
| Sodium Benzoate | NaBenzoate or NaBz |
| Sodium Carbonate | NaCarb |
| Sodium Bicarbonate | BiCarb |
| Calcium Benzoate | CaBenzoate |
| Polyoxyethylene Sorbitan Monooleate (20 moles of ethoxylation, Tween ® 80[1]) | Surf. A |
| Block copolymer of ethylene oxide and propylene oxide, (Pluronic ® F68[2]) | Surf. B |
| Glyceryl dioleate | GDO |
| Polyoxyethylene Stearate, 23 moles of ethoxylation | POE (23) stearate |
| Polyethylene Glycol Distearate, average MW of PEG 1540 | PEG 1540 distearate |
| Polyethylene Glycol, average MW 6000 | PEG 6000 |
| Polyoxyethylene Sorbitan Monostearate | POE (20) sorbitan monostearate |
| Carbonate Buffered Saline (pH 9.4) | CBS |
| Polyethylene glycol | PEG |
| Mixture of caprylic, capric, lauric and caproic triglycerides | Miglyol ® 812[3] |

[1]Trademark of ICI Americas, Inc.
[2]Trademark of BASF Wyandotte Corp.
[3]Trademark of Dynamit Nobel

TABLE II

| | | Microsphere Compositions | | |
| --- | --- | --- | --- | --- |
| | | | Additives (%) | |
| Composition # | Matrix | BGH (%) | Buffer/Pres. | Surfactant |
| 1 | GMS | 2.5 | — | — |
| 2 | | 7.5 | — | — |
| 3 | | 20 | — | — |
| 4 | GMS/soya oil | 20 | — | — |
| 5 | | 30 | — | — |

TABLE II-continued

Microsphere Compositions

| Composition # | Matrix | BGH (%) | Additives (%) Buffer/Pres. | Surfactant |
|---|---|---|---|---|
| 6 | GDS | 10 | — | — |
| 7 | | 10 | NaLaurate(1.4) | — |
| 8 | | 25 | NaBenzoate(1.6) | Surf. B(0.12) |
| 9 | | 25 | NaCarb/bicarb(1.3) | Surf. A(0.18) |
| 10 | GTS/GDS (19:1) | 10 | — | — |
| 11 | | 15 | — | — |
| 12 | | 10 | NaBenzoate(0.6) | Surf. B(0.05) |
| 13 | GTS/GDS (9:1) | 10 | — | Surf. B(0.1) |
| 14 | | 10 | NaBenzoate(0.6) | Surf. B(0.05) |
| 15 | | 18 | — | — |
| 16 | | 15 | — | — |
| 17 | | 15 | CaBenzoate(1.1) | — |
| 18 | GTS/beeswax (9:1) | 7.5 | — | — |
| 19 | | 15 | — | — |
| 20 | GTS/GMS (19:1) | 7.5 | — | — |
| 21 | | 12 | — | — |
| 22 | | 15 | NaBenzoate(1.4) | — |
| 23 | GTS/soya oil (19:1) | 7.5 | — | — |
| 24 | (39:1) | 7.5 | — | — |
| 25 | GMS/carnauba (1:2) | 20 | — | — |
| 26 | GTS | 7.5 | — | — |
| 27 | | 10 | — | — |
| 28 | | 15 | — | — |
| 29 | | 10 | NaBenzoate(0.8) | — |
| 30 | | 10 | — | Surf. B(0.05) |
| 31 | | 10 | — | Surf. B(0.2) |
| 32 | | 25 | — | — |
| 33 | | 25 | NaBenzoate(0.75) | Surf. B(0.12) |
| 34 | | 25 | NaBenzoate(1.6) | Surf. B(0.12) |
| 35 | | 25 | NaBenzoate(3.2) | Surf. B(0.12) |
| 36 | | 25 | NaBenzoate(1.6) | — |
| 37 | | 25 | — | Surf. B(0.12) |
| 38 | | 25 | — | Surf. B(0.24) |
| 39 | | 25 | — | Surf. A(0.12) |
| 40 | | 25 | — | Surf. A(0.24) |
| 41 | | 25 | — | Surf. A(0.48) |
| 42 | | 25 | NaCarb/bicarb(1.2) | — |
| 43 | | 25 | NaCarb/bicarb(1.2) | Surf. A(0.12) |
| 44 | | 33 | NaCarb/bicarb(2.1) | Surf. A(0.17) |
| 45 | | 33 | NaBenzoate(2.1) | Surf. B(0.17) |
| 46 | | 33 | NaBenzoate(2.1) | Surf. A(0.17) |
| 47 | GTL | 33 | NaBenzoate(2.1) | Surf. A(0.17) |
| 48 | GTS/GDS (12:1) | 15 | CaBenzoate(1.1) | — |
| 49 | Beeswax/Soya Oil (2:1) | 30 | — | — |
| 50 | GMS/Soya Oil (47.25/24) | 25 | — | Sorbitan monoleate (3.75) |
| 51 | GMS | 20 | — | PEG 1540 distearate(16.0) |
| 52 | Diethylene glycol monostearate | 25 | — | — |
| 53 | GMS | 10 | — | POE(23) stearate (9.0) |
| 54 | GMS | 20 | — | PEG 6000(9.0) |
| 55 | GMS | 20 | — | PEG 6000(4.0) |
| 56 | GMS | 20 | — | PEG 6000(0.8) |
| 57 | GMS | 20 | — | POE (20) Sorbitan monostearate (4.0) |
| 58 | GMS | 20 | — | PEG 400 distearate (8.0) |
| 59 | GMS | 20 | — | PEG 400 distearate (1.57) |
| 60 | GMS | 30 | — | Sorbitan tristearate (7) |

EXAMPLE 2

Effectiveness injectable microspheres in various vehicles

The efficacy of various injectable compositions of microspheres in different vehicles is determined utilizing a hypophysectomized (hypox) rat assay. The hypophysectomized rat does not produce its own growth hormone and is sensitive to injected bovine growth hormone. The response measured is growth over a period of time such as 10 days.

Each of the hypox albino rats (Taconic Farms, Sprague Dawley derived) is injected with a sufficient quantity of microsphere compositions prepared in Example 1 to provide a 10-day dose of 800 micrograms (80 micrograms/day) of bovine growth hormone in 0.2 ml of the vehicles listed in Table III below.

TABLE III

| Vehicle Components | |
|---|---|
| Name | Designation |
| Glyceryl Dioleate | GDO |
| Saline | SAL |
| Capric/Caprylic Triglycerides | C/C |
| Soya Oil | Soya Oil |
| Diethyl Succinate | DES |
| Aluminum Monostearate Gel | Gel |
| Carbowax (Thickener) | THX |

Test Procedures

Prior to the test, the animals are weighed and the animals to be used for the test are selected based on body weight. Only those animals whose body weights are one standard deviation from the mean body weight of the group are selected. The resulting group is then randomly divided into treatment groups consisting of eight rats/group by a computer generated randomization procedure. The test animals are then transferred to a clean cage and housed four rats/cage. On the initial day of the study the test animals are weighed and any animals with excessive weight gain or loss ($\pm 5$ grams) are replaced. The animals are then assigned to test groups and treated.

At the end of the ten-day test period, total weight gain for each animal is recorded and the average weight gain per rat for each treatment determined. The results of these experiments, which are summarized in Table IV below, demonstrate the effectiveness of injectable composition of microspheres with various vehicles.

TABLE IV

Efficacy of Injectable Microspheres in Various Vehicles

| Microsphere Composition of Example[1] | Vehicle | 10-Day Growth (Grams) |
|---|---|---|
| 48 | GDO | 19.5 |
| 32 | GDO | 17.9 |
| 18 | SAL | 19.4 |
| 16 | GDO | 18.5 |
| 12 | C/C | 19.8 |
| 16 | GDO | 15.5 |
| 12 | SAL | 16.6 |
| 27 | SAL | 17.4 |
| 16 | C/C | 14.0 |
| 16 | GDO/DES (4:1) | 13.7 |
| 32 | Soya Oil | 15.6 |
| 39 | Soya Oil | 16.0 |
| 8 | 8% Gel/Soya Oil | 14.0 |
| 34 | 8% Gel/Soya Oil | 8.0 |
| 42 | Soya Oil | 12.6 |
| 43 | Soya Oil | 8.0 |
| 34 | 0.5% THX/Soya Oil | 17.0 |
| 37 | 0.5% THX/Soya Oil | 14.0 |
| 36 | 0.5% THX/Soya Oil | 13.6 |
| 33 | 0.5% THX/Soya Oil | 16.8 |
| 35 | 0.5% THX/Soya Oil | 14.5 |
| | negative controls* | $0.7 \pm 3.15$ |

*average growth of 22 negative control groups (no treatment)

EXAMPLE 3

Evaluation of growth hormone microsphere compositions in dairy cows

Lactating cows are divided into groups of three to eight animals. Throughout the test, all cows are fed the same ration of corn silage, alfalfa hay and dairy concentrate adequate to produce 25 kg to 30 kg of milk per day. The cows are not treated for two weeks and daily milk production and bovine growth hormone blood levels obtained for each group of animals. The experimental or control treatments listed in Table V below are then administered during the treatment period. Growth hormone levels in the blood of the animals is determined by standard RIA techniques periodically and milk production levels are recorded daily. The results of these experiments, which are summarized in Tables VI and VII below, demonstrate the effectiveness of the compositions of the invention for increasing milk production, and for increasing and maintaining elevated growth hormone levels in the blood respectively.

TABLE V

Formulations Used in Dairy Cows

| # | Microsphere Composition % bGH | Preservative/Stabilizer/ Surfactant | Matrix | Vehicle | MS/Vehicle Ratio | bGH Dose | |
|---|---|---|---|---|---|---|---|
| A | — | — | — | CBS | — | 12.5 mg | for 28 days |
| B | 24.5 | NaBz(1.6)/Surf. B(0.12) | GTS(73.8) | Miglyol/ Soya Oil (4/1) | 1/2.5 | 350 mg | day 0, day 14 |
| C | 24.5 | NaBz(1.6)/Surf. B(0.12) | GTS(73.8) | Miglyol/ Soya Oil (4/1) | 1/2.5 | 525 mg | day 0, day 14 |
| D | — | — | — | CBS | | 25 mg | for 28 days |
| E | 24.5 | NaCarb/Bicarb (1/2)/ Surf. A(0.12) | GDS(74.3) | Soya Oil | 1/2.5 | 350 mg | day 0, day 14 |
| F | 24.5 | NaBz(1.6)/Surf. B(0.12) | GTS(73.8) | Miglyol/ Soya Oil (4/1) | 1/2.5 | 350 mg | day 0, day 14 |
| G | — | — | — | CBS | | 25 mg | for 14 days |
| H | 24.5 | NaBz(1.6)/Surf. B(0.12) | GTS(73.8) | Miglyol/ Soya Oil | 1/2.5 | 175 mg | day 0, day 7 |
| I | 24.5 | NaBz(1.6)/Surf. B(0.12) | GTS(73.8) | Miglyol/ Soya Oil (4/1) | 1/2.5 | 350 mg | day 0 |
| J | — | — | — | CBS | — | 25 mg | for 28 days |
| K | 7.5 | — | GTS/Beeswax | saline | 1/5 | 750 mg | day 0 |

TABLE V-continued

Formulations Used in Dairy Cows

| # | bGH | Microsphere Composition % Preservative/Stabilizer/ Surfactant | Matrix | Vehicle | MS/Vehicle Ratio | bGH Dose |
|---|---|---|---|---|---|---|
| | | (9/1)(92.5) | | | | |

TABLE VI

Average Milk Production Increases from Dairy Cow Experiments

| Formulation Number | Percent Increase in Milk Production Compared to Undosed Control Cows | | | |
|---|---|---|---|---|
| | Week 1 | Week 2 | Week 3 | Week 4 |
| A | 10.5 | 13.9 | 12.3 | 14.7 |
| B | 16.4 | 21.1 | 19.2 | 20.8 |
| C | 17.8 | 19.4 | 17.3 | 19.3 |
| D | 9.2 | 16.7 | 15.6 | 15.8 |
| E | 8.4 | 7.3 | 16.0 | 4.0 |
| F | 6.7 | 4.5 | 13.8 | 9.8 |
| G | 9.6 | 19.3 | 9.5 | 3.7 |
| H | 7.4 | 14.0 | 6.0 | 4.0 |
| I | 11.1 | 10.6 | 4.1 | 6.3 |
| J | 14.2 | 13.1 | 20.1 | 24.5 |
| K | 17.7 | 4.9 | 3.6 | 0.1 |

TABLE VII

Average Plasma bGH Concentration (ng/mL by Radioimmunoassay) for Dairy Cow Experiments

| Elapsed Time (Days) | Formulation Number | | | | | |
|---|---|---|---|---|---|---|
| | A* | B | C | D* | E | F |
| −24 Hr | 1.3 | 1.3 | 1.5 | 1.2 | 1.0 | 1.1 |
| 0 Hr | 1.4 | 1.2** | 1.4** | 1.1 | 1.0** | 1.1** |
| 3 Hr | 6.1 | 2.0 | 3.3 | 20.0 | 25.6 | 1.1 |
| 6 Hr | 5.2 | 6.9 | 8.5 | 7.2 | 50.1 | 1.2 |
| 1 Day | 2.6 | 30.8 | 37.6 | 1.5 | 13.5 | 13.8 |
| 2 Day | 2.4 | 9.7 | 20.1 | 3.7 | 7.2 | 8.4 |
| 5 Day | 2.8 | 6.7 | 9.2 | 3.9 | 8.2 | 5.8 |
| 7 Day | 2.9 | 7.3 | 9.9 | 7.4 | 8.2 | 6.9 |
| 9 Day | 3.4 | 7.2 | 9.8 | 7.8 | 8.5 | 7.3 |
| 12 Day | 3.7 | 6.4 | 8.5 | 3.8 | 2.9 | 1.8 |
| 14 Day | 2.7 | 4.3** | 5.6** | 4.0 | 2.4** | 1.5** |
| 16 Day | 3.2 | 14.2 | 21.2 | 5.5 | 45.7 | 15.7 |
| 19 Day | 3.9 | 9.9 | 11.2 | 7.2 | 9.6 | 9.0 |
| 21 Day | 3.2 | 14.7 | 12.9 | 6.4 | 8.1 | 7.5 |
| 23 Day | 2.4 | 9.5 | 8.0 | 6.3 | 7.8 | 6.1 |
| 26 Day | 2.5 | 7.8 | 8.4 | 5.4 | 5.4 | 3.7 |
| 28 Day | 2.2 | 4.6 | 6.1 | 4.9 | 5.0 | 2.8 |

TABLE VII-continued

Average Plasma bGH Concentration (ng/mL by Radioimmunoassay) for Dairy Cow Experiments

| Time (Days) | Number | | Time (Days) | Number | | |
|---|---|---|---|---|---|---|
| | J* | K | | G* | H | I |
| −24 Hr | 2.3 | 5.2 | −24 Hr | 3.0 | 5.3 | 3.1 |
| 0 Hr | 4.1 | 7.3** | 0 Hr | 2.9 | 3.8** | 3.5** |
| 1 Hr | 12.2 | 34.5 | 3 Hr | 15.0 | 4.6 | 3.8 |
| 2 Hr | 15.3 | 57.2 | 6 Hr | 10.4 | 3.7 | 4.7 |
| 4 Hr | 15.8 | 127.8 | 1 Day | 5.1 | 10.2 | 31.5 |
| 6 hr | 12.7 | 102.7 | 2 Days | 4.7 | 7.8 | 24.5 |
| 1 Day | 4.4 | 107.7 | 3 Days | 4.2 | 6.2 | 8.4 |
| 2 Days | 4.0 | 33.3 | 4 Days | 4.8 | 6.7 | 9.2 |
| 3 Days | 4.1 | 15.3 | 5 Days | 4.3 | 6.5 | 9.7 |
| 4 Days | 4.7 | 13.1 | 6 Days | 6.1 | 8.0 | 11.2 |
| 6 Days | 5.7 | 15.8 | 7 Days | 6.2 | 9.6** | 13.1 |
| 8 Days | 6.0 | 17.6 | 8 Days | 6.0 | 18.0 | 11.9 |
| 11 Days | 6.7 | 34.5 | 10 Days | 6.5 | 16.8 | 13.1 |
| | | | 13 Days | 7.9 | 18.6 | 11.8 |
| | | | 17 Days | 5.2 | 16.5 | 11.0 |
| | | | 20 Days | 5.7 | 17.3 | 12.6 |

*note:
blood samples taken prior to daily injection
**Injections administered on the morning of these days after the blood sample was taken.

EXAMPLE 4

Sustained release of compositions of the invention in sheep

Utilizing essentially the same procedure as Example 3, the compositions prepared in Example 1 and listed in Table VIII below are administered to groups of sheep (three animals per group). The animals are dosed with 3 mg bGH equivalents of microspheres per kg body weight. Daily blood samples are obtained for a 30 day period and assayed for bGH blood levels as previously described. The results of these experiments which are summarized in Table VIII below, demonstrate the effectiveness of the compositions of the invention for maintaining elevated levels of growth hormone in the blood for extended periods of time.

TABLE VIII

Plasma levels by RIA in Sheep

| Composition # | Vehicle | Plasma level data | | | |
|---|---|---|---|---|---|
| | | Highest Level | | Duration in (days) | |
| | | ng/ml | (hr) | >10 ng/mL | >5 ng/mL |
| 13 | 5% PEG(18, 500MW) in Saline | 200 | 4 | 1 | 2 |
| 14 | 5% PEG(18, 500MW) in Saline | 300 | 4 | 2 | 5 |
| 15 | 5% PEG(5000)MW in Saline | 140 | 6 | 1 | 2 |
| 15 | GDO | 50 | 6–24 | 2 | 3 |
| 32 | Miglyol 812 | 30 | 24 | 13 | 20 |
| 32 | Soya oil | 10 | 24 | >20 | >27 |
| 34 | Soya oil | 50 | 24 | 10 | 22 |
| 32 | GDO | 50 | 24 | 10 | 13 |
| 34 | Miglyol 812 | 100 | 6–24 | 10 | 22 |
| 8 | Soya oil | 290 | 24 | 10 | >24 |
| 8 | Soya oil/Miglyol 812 (1:1) | 290 | 24 | 6 | 13 |
| 34 | Soya oil/Miglyol 812 (1:1) | — | 4–24 | 10 | >20 |

TABLE VIII-continued

| | | Plasma levels by RIA in Sheep | | | |
| | | Plasma level data | | | |
| | | Highest Level | | Duration in (days) | |
| Composition # | Vehicle | ng/ml | (hr) | >10 ng/mL | >5 ng/mL |
| 45 | Soya oil/Miglyol 812 (1:1) | — | 4–24 | 3 | 6 |
| 46 | Soya oil/Miglyol 812 (1:1) | — | 4–24 | 3 | 4 |
| 47 | Soya oil/Miglyol 812 (1:1) | — | 4–24 | 3 | 10 |
| 43 | Soya oil/Miglyol 812 (1:1) | — | 4–24 | 3 | 10 |

EXAMPLE 5

Efficacy of bovine growth hormone mixture of the invention in dairy cows.

A mixture of bovine growth hormone containing sodium benzoate (7% w/w) and a block copolymer of ethylene oxide and propylene oxide (0.5% w/w) is prepared by the spray drying procedure described in example 1.1.

The thus prepared mixture (7.28 g) is added to a stirred solution of glyceryl tristearate (19.5 g) in a 4/1 w/w mixture of, a mixture of caprylic, capric, lauric and caprioc triglycerides (Miglyol ® 812)³/soya oil (71 mL), at 75° C. to 80° C. The mixture is stirred at 75° C. to 80° C. until it is homogeneous and is then cooled. The resulting composition which is comprised on a weight basis of: bovine growth hormone 6.96%, sodium benzoate 0.51%, surfactant (block copolymer) 0.03% and vehicle 73.0% is administered to lactating cows by the procedure of example 3. The results of these experiments which are summarized in Table IX below demonstrate the effectiveness of these compositions for increasing milk production for extended periods of time

TABLE IX

| Average Milk Production Increases Compared to Undosed Control Cows | |
| --- | --- |
| % increase Week 1 | % increase Week 2 |
| 15.7 | 12.0 |

What is claimed is:

1. A microsphere composition comprising on a weight basis about 30% to 95% of a fat or wax or mixture thereof and about 2% to 70% of a biologically active protein, peptide or polypeptide.

2. A microsphere composition according to claim 1 comprising on a weight basis about 40% to 95% of a wax or a fat or mixtures thereof; about 5% to 40% of a growth hormone, somatomedin, growth factor or biologically active fragment or derivative thereof; 0% to about 20% of surfactant, preservative, stabilizer, salt, buffer or mixture thereof; wherein the weight average particle size of the microsphere composition is in a range of 25 microns to 300 microns.

3. A microsphere composition according to claim 2 wherein the growth hormone is bovine, porcine or avian growth hormone.

4. A microsphere composition according to claim 3 comprising on a weight basis about 20% to 40% of bovine growth hormone; and about 55% to 79% glyceryl tristearate.

5. A microsphere composition according to claim 4 for parenteral administration and slow release in a pharmaceutically and pharmacologically acceptable liquid vehicle.

6. A microsphere composition comprising on a weight basis about 20% to 40% bovine growth hormone; about 55% to 79% glyceryl tristearate; 0 to about 0.2% microbiological preservative; 0 to about 1% nonionic surfactant; and 0 to about 2% sodium benzoate.

7. A method for increasing milk production in lactating animals comprising parenterally
administering to the animal a microsphere composition comprising on a weight basis about 30% to 95% fat or wax or mixtures thereof; and about 2% to 70% of a growth hormone, somatomedin, growth factor or biologically active fragment or derivative thereof; wherein the microsphere is dispersed in a pharmaceutically and pharmacologically acceptable liquid vehicle.

8. A method according to claim 7 wherein the microsphere comprises on a weight basis about 40% to 95% of a wax or fat or mixtures thereof; about 5% to 40% of animal growth hormone, 0% to about 20% of surfactant, preservative, stabilizer, salt, buffer or mixture thereof and the weight average particle size of the microspheres is in a range of 25 microns to 300 microns.

9. A method according to claim 8 wherein the microsphere comprises on a weight basis about 20% to 40% of bovine growth hormone; about 55% to 79% glyceryl tristearate and the microsphere vehicle is a neutral mono-, di-, triglyceride liquid or mixtures thereof.

10. A method for increasing weight gains in animals comprising parenterally
administering to the animal a microsphere composition comprising on a weight basis about 30% to 95% fat or wax or mixtures thereof; and about 2% to 70% of a growth hormone, somatomedin, growth factor or biologically active fragment or derivative thereof; wherein the microsphere is dispersed in a pharmaceutically and pharmacologically acceptable liquid vehicle.

11. A method according to claim 10 wherein the microsphere comprises on a weight basis about 40% to 95% of fat or wax or mixtures thereof; about 5% to 40% of animal growth hormone; 0% to about 20% surfactant, preservative, stabilizer, salt, buffer or mixture thereof; and the weight average particle size of the microspheres is in a range of 25 microns to 300 microns.

12. A method according to claim 11 wherein the microsphere comprises on a weight basis about 20% to 40% of bovine growth hormone; about 55% to 79% glyceryl tristearate; and the microsphere vehicle is a neutral mono-, di-, or triglyceride liquid or mixtures thereof.

13. A method for elevating and maintaining elevated blood levels of a biologically active protein, peptide or polypeptide, improving feed efficiency, increasing growth rate, increasing muscle size, decreasing body fat and improving lean meat to fat ratio in an animal comprising parenterally administering to the animal a microsphere composition comprising on a weight basis about 30% to 95% fat or wax or mixtures thereof; and about 2% to 70% of a growth hormone, somatomedin, growth factor or biologically active fragment or derivative thereof; wherein the microsphere is dispersed in a pharmaceutically and pharmacologically acceptable liquid vehicle.

14. A method according to claim 13 wherein the microsphere comprises on a weight basis about 40% to 95% of a wax or a fat or mixtures thereof; about 5% to 40% of animal growth hormone; 0% to about 20% of surfactant preservative, stabilizer, salt, buffer or mixture thereof and the weight average particle size of the microspheres is in a range of 25 microns to 300 microns.

15. A method according to claim 14 wherein the microsphere comprises on a weight basis about 20% to 40% of bovine growth hormone; about 55% to 79% glyceryl tristearate; and the microsphere vehicle is a neutral mono-, di-, or triglyceride liquid or mixtures thereof.

16. A slow release composition comprising a fat or wax or mixture thereof and a biologically active protein, peptide or polypeptide dispersed in a pharmaceutically and pharmacologically acceptable liquid vehicle.

17. A composition according to claim 16 characterized by heating about 1% to 30% of growth hormone, somatomedin, growth factor or biologically active fragment or derivative thereof; about 5% to 60% of fat or wax or mixtures thereof; 0% to about 15% of surfactant, preservative, stabilizer, salt, buffer or mixture thereof; and sufficient oil to total 100% to obtain a homogeneous mixture; and cooling said mixture to ambient temperature to form said composition.

18. A composition according to claim 17 wherein the growth hormone is bovine, porcine or avian growth hormone.

19. A composition according to claim 18 comprising on a weight basis about 5% to 27% of bovine growth hormone; about 10% to 48% of glyceryl tristearate; 0% to about 0.2% microbiological preservative and 0% to about 1% non-ionic surfactant; and sufficient neutral mono-, di-, or triglyceride liquid or mixtures thereof to total 100%.

20. A method for increasing milk production in lactating animals comprising parenterally administering to the animal a biologically active slow release composition characterized by heating about 1% to 30% of growth hormone, somatomedin, growth factor or biologically active fragment or derivative thereof; about 5% to 60% of fat or wax or mixtures thereof; 0% to about 15% of surfactant, preservative, stabilizer, salt, buffer or mixture thereof; and sufficient oil to total 100% to obtain a homogeneous mixture; and cooling said mixture to ambient temperature to form said composition.

21. A method for increasing milk production in animals according to claim 20 wherein the composition comprises on a weight basis about 5% to 27% bovine growth hormone; about 10% to 48% glyceryl tristearate; 0% to about 0.2% microbiological preservative and 0% to about 1% non-ionic surfactant; and sufficient neutral mono-, di-, or triglyceride liquid or mixtures thereof to total 100%.

22. A method for increasing weight gains comprising parenterally administering to the animal a biologically active slow release composition characterized by heating about 1% to 30% of growth hormone, somatomedin, growth factor or biologically active fragment or derivative thereof; about 5% to 60% of fat or wax or mixtures thereof; 0% to about 15% of surfactant, preservative, stabilizer, salt, buffer or mixture thereof; and sufficient oil to total 100% to obtain a homogeneous mixture; and cooling said mixture to ambient temperature to form said composition.

23. A method according to claim 22 wherein the composition comprises on a weight basis about 5% to 27% bovine growth hormone; about 10% to 48% of glyceryl tristearate; 0% to about 0.2% microbiological preservative and 0% to about 1% non-ionic surfactant; and sufficient neutral mono-, di, or triglyceride liquid or mixtures thereof to total 100%.

24. A method for elevating and maintaining elevated blood levels of a biologically active protein, peptide or polypeptide, improving feed efficiency, increasing growth rate, increasing muscle size, decreasing body fat and improving lean meat to fat ratio in an animal comprising parenterally administering to the animal a biologically active slow release composition characterized by heating about 1% to 30% of growth hormone, somatomedin, growth factor or biologically active fragment or derivative thereof; about 5% to 60% of fat or wax or mixtures thereof; 0% to about 15% of surfactant, preservative, stabilizer, salt, buffer or mixture thereof; and sufficient oil to total 100% to obtain a homogeneous mixture; and cooling said mixture to ambient temperature to form said composition.

25. A method according to claim 24 wherein the composition comprises on a weight basis about 5% to 27% bovine growth hormone; about 10% to 48% of glyceryl tristearate; 0% to about 0.2% microbiological preservative and 0% to about 1% non-ionic surfactant; and sufficient neutral mono-, di-, or triglyceride liquid or mixtures thereof to total 100%.

* * * * *

UNITED STATES PATENT OFFICE
CERTIFICATE OF CORRECTION

Patent No. 4,837,381             Dated  June 6, 1989

Inventor(s)  William Steber et al.

It is certified that error appears in the above-identified patent and that said Letters Patent is hereby corrected as shown below:

Claim 1, line 47, "microsphere" should be deleted.

Claim 1, line 48, after "weight basis about" -- 2% to 70% growth hormone, somatomedin, growth factor or biologically active fragment or derivative thereof uniformly dispersed in about -- should be inserted and, after "95%, "of" should be deleted.

Claim 1, line 49, after "thereof" "and about 2% to 70% of a biologically active protein, peptide or polypeptide" should be deleted.

Claim 1, line 49, after "thereof -- , wherein said composition is provided in the form of microspheres -- should be inserted.

Claim 2, line 51, "microsphere" should be deleted.

Claim 2, line 52, "of a" should be deleted.

Claim 2, line 53, after "wax or", "a" should be deleted; after "fat or", "mixtures" should be deleted and -- mixture -- inserted; after "40%, "of a" should be deleted.

Claim 2, line 56, after "20%", "of" should be deleted.

Claim 2, line 58, "microsphere" should be deleted.

UNITED STATES PATENT OFFICE
CERTIFICATE OF CORRECTION

Patent No. 4,837,381　　　　　　Dated June 6, 1989

Inventor(s) William Steber et al.

It is certified that error appears in the above-identified patent and that said Letters Patent is hereby corrected as shown below:

Claim 3, line 60, "microsphere" should be deleted.

Claim 4, line 63, "microsphere" should be deleted.

Claim 4, line 64, after "40%", "of" should be deleted.

Claim 5, line 67, "microsphere" should be deleted.

Claim 6, line 1, "microsphere" should be deleted.

Claim 7, line 24, after "administering to", "the" should be deleted and -- an -- inserted. Same line, "microsphere" should be deleted.

Claim 7, lines 25 and 26, after "basis", "about 30% to 95% fat or wax or mixtures thereof; and" should be deleted.

Claim 7, line 27, after "70%", "of a" should be deleted.

Claim 7, line 29, after "thereof" the ";" should be deleted and -- uniformly dispersed in about 30% to 95% fat or wax or mixture thereof, -- should be inserted. Same line, "the microsphere is" should be deleted and -- said composition is provided in the form of microspheres -- should be inserted.

Claim 8, lines 32 and 33, "microsphere" should be deleted and -- composition -- should be inserted.

UNITED STATES PATENT OFFICE
CERTIFICATE OF CORRECTION

Patent No. 4,837,381          Dated   June 6, 1989

Inventor(s)   William Steber et al.

It is certified that error appears in the above-identified patent and that said Letters Patent is hereby corrected as shown below:

Claim 8, line 34, before "wax", "of a" should be deleted; "mixtures" should be deleted and -- mixture -- inserted; after "40%", "of" should be deleted.

Claim 8, line 35, after "20%", "of" should be deleted.

Claim 8, lines 37 and 38, "microspheres" should be deleted and -- composition -- should be inserted.

Claim 9, lines 39 and 40, "microsphere" should be deleted and -- composition -- should be inserted.

Claim 9, line 41, before "bovine", "of" should be deleted.

Claim 9, line 42, "microsphere" should be deleted.

Claim 9, line 43, after "di-,", -- or -- should be inserted.

Claim 10, line 46, "microsphere" should be deleted.

Claim 10, lines 47 and 48, "about 30% to 95% fat or wax or mixtures thereof; and" should be deleted.

Claim 10, line 49, after "to 70%", "of a" should be deleted.

Claim 10, line 51, after "thereof", the ";" should be deleted and  -- uniformly dispersed in about

UNITED STATES PATENT OFFICE
CERTIFICATE OF CORRECTION

Patent No. 4,837,381  Dated June 6, 1989

Inventor(s) William Steber et al.

It is certified that error appears in the above-identified patent and that said Letters Patent is hereby corrected as shown below:

30% to 95% fat or wax or mixture thereof, -- should be inserted; after "wherein", "the microsphere is" should be deleted and -- said composition is provided in the form of microspheres -- should be inserted.

Claim 11, line 55, "microsphere" should be deleted and -- composition -- should be inserted.

Claim 11, after "95%" "of" should be deleted; "mixtures" should be deleted and -- mixture -- should be inserted.

Claim 11, line 57, before "animal", delete "of".

Claim 11, line 60, "delete "microsphere" and insert -- composition --.

Claim 12, line 62, "microspheres" should be deleted and -- composition -- should be inserted.

Claim 12, line 63, after "40%" "of" should be deleted.

Claim 12, line 64, "microsphere" should be deleted.

Claim 13 (Column 14, line 68 and Column 15, line 1) "biologically active protein, peptide or polypeptide" should be deleted and -- growth hormone, somatomedin, growth factor or biologically active fragment or derivative thereof, -- should be inserted.

UNITED STATES PATENT OFFICE
CERTIFICATE OF CORRECTION

Patent No. 4,837,381          Dated  June 6, 1989

Inventor(s) William Steber et al.

It is certified that error appears in the above-identified patent and that said Letters Patent is hereby corrected as shown below:

Claim 13, line 5, "microsphere" should be deleted.

Claim 13, lines 6 and 7, after "basis", "about 30% to 95% fat or wax or mixtures thereof; and" should be deleted.

Claim 13, line 8, after "70%", "of a" should be deleted.

Claim 13, line 10, after thereof, the ";" should be deleted and -- uniformly dispersed in about 30% to 95% fat or wax or mixture thereof, -- should be inserted. Same line, "the microsphere is" should be deleted and -- said composition is provided in the form of microspheres -- should be inserted.

Claim 14, line 14, "microsphere" should be deleted and -- composition -- should be inserted.

Claim 14, line 15, after "95%", "of a" should be deleted. Same line, "mixtures" should be deleted and -- mixture -- should be inserted.

Claim 14, line 16, after "40%", "of" should be deleted, after "20%" "of" should be deleted Claim 14, line 17, after "surfactant", a comma (,) should be inserted.

Claim 14, lines 18 and 19, "microspheres" should be deleted and -- composition -- should be inserted.

UNITED STATES PATENT OFFICE
CERTIFICATE OF CORRECTION

Patent No. 4,837,381  Dated  June 6, 1989

Inventor(s)  William Steber et al.

It is certified that error appears in the above-identified patent and that said Letters Patent is hereby corrected as shown below:

Claim 15, line 21, "microsphere" should be deleted and -- composition -- should be inserted.

Claim 15, line 22, after "40%", "of" should be deleted.

Claim 15, line 23, "microsphere" should be deleted.

Claim 16, line 26, after "comprising", "a" should be deleted and -- growth hormone, somatomedin, growth factor or biologically active fragment or derivative thereof dispersed in -- should be inserted.

Claim 16, lines 27 and 28. "and a biologically active protein, peptide or polypeptide" should be deleted.

Claim 17, line 31, after "30%", "of" should be deleted.

Claim 17, line 33, after "60%", "of" should be deleted.

Claim 17, line 34, after "wax or", "mixtures" should be deleted and -- mixture -- should be inserted. Same line, after "15%", "of" should be deleted.

Claim 20, line 53, after "30%", "of" should be deleted.

UNITED STATES PATENT OFFICE
CERTIFICATE OF CORRECTION

Patent No. 4,837,381                    Dated  June 6, 1989

Inventor(s) William Steber et al.

It is certified that error appears in the above-identified patent and that said Letters Patent is hereby corrected as shown below:

Claim 20, line 55, after "60%", "of" should be deleted.

Claim 20, line 56, "mixtures" should be deleted and -- mixture -- inserted. Same line, after "15%", "of" should be deleted.

Claim 22, line 17, after "30%", "of" should be deleted.

Claim 22, line 19, after "60%", "of" should be deleted.

Claim 22, line 20, "mixtures" should be deleted and -- mixture -- should be inserted. Same line, after "15%", "of" should be deleted.

Claim 24, lines 34 and 35, "a biologically active protein, peptide or polypeptide," should be deleted and -- growth hormone, somatomedin, growth factor or biologically active fragment or derivative thereof, -- should be inserted.

Claim 24, line 41, after "30%", "of" should be deleted.

Claim 24, line 43, after "60%", "of" should be deleted.

UNITED STATES PATENT OFFICE
CERTIFICATE OF CORRECTION

Patent No. 4,837,381  Dated June 6, 1989

Inventor(s) William Steber et al.

It is certified that error appears in the above-identified patent and that said Letters Patent is hereby corrected as shown below:

Claim 24, line 44, "mixtures" should be deleted and -- mixture -- should be inserted. Same line, after "15%", "of" should be deleted.

Signed and Sealed this

Tenth Day of July, 1990

Attest:

HARRY F. MANBECK, JR.

*Attesting Officer*  *Commissioner of Patents and Trademarks*